(12) United States Patent
Sigman et al.

(10) Patent No.: US 8,263,774 B2
(45) Date of Patent: Sep. 11, 2012

(54) QUINOLINE-OXAZOLINE COMPOUNDS AND THEIR USE IN OXIDATION SYNTHESIS

(75) Inventors: Matthew Scott Sigman, Salt Lake City, UT (US); Brian William Michel, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 360 days.

(21) Appl. No.: 12/553,352

(22) Filed: Sep. 3, 2009

(65) Prior Publication Data

US 2011/0054176 A1     Mar. 3, 2011

(51) Int. Cl.
C07D 215/38     (2006.01)
(52) U.S. Cl. .................................. 546/144; 546/167
(58) Field of Classification Search .................. 546/144, 546/167
See application file for complete search history.

(56) References Cited

U.S. PATENT DOCUMENTS

| | | | |
|---|---|---|---|
| 4,661,642 A | 4/1987 | Feringa | |
| 4,723,041 A | 2/1988 | Vasilevskis | |
| 7,026,266 B2 | 4/2006 | Chaudhari et al. | |
| 7,166,754 B2 | 1/2007 | Ferreira et al. | |

OTHER PUBLICATIONS

Perch, J Org Chem, vol. 65, pp. 3836-3845, 2000.*
Park, Tetrahedron: Asymmetry, vol. 10, pp. 1903-1911, 1999.*
Hortala, Tetrahedron Letters, vol. 43, pp. 1027-1029, 2002.*
Dondondi, CA 110:57552, abstract only of Synthesis, VOl 8, pp. 693-696, 1987.*
Dondondi, CA 107:77670, abstract only of Tetrahedron Letters, vol. 27(43), pp. 5269-5270, 1986.*
Delapierre, Tetrahedron: Asymmetry, vol. 12, pp. 1345-1352, 2001.*
Chelucci, Tetrahedron, VOl 56, pp. 2889-2893, 2000.*
Chelucci, Tetrahedron: Asymmetry, vol. 10, pp. 543-550, 1990.*
Brunner, CA115:256278, abstract only of Tetrahedron: Asymmetry, vol. 2(9), pp. 919-930, 1991.*
Brunner, Tetrahedron: Asymmetry, VOl 14, pp. 2177-2187, 2003.*
Bremberg, CA 133:207598, abstract only of Synthesis, VOl 7, pp. 1004-1008, 2000.*
Bremberg, Tetrahedron: Asymmetry, vol. 9, pp. 3437-3443, 1998.*
Rhodium; Improved Wacker Oxidation of Alkenes to Ketones, J. Org. Chem.; 1990; 2924-2927; vol. 55.
Sigma-Aldrich MSDS for Product #713929, Dichloro[2-(4,5-Dihydro-2-oxazoly)quinoline]palladium(II), Revision Date Jun. 8, 2010.
Sigma-Aldrich MSDS for Product #713910, 2-(4,5-Dihydro-2-oxazolyl)quinoline, Revision date Jun. 8, 2010.
Michel et al.; A General and Efficient Catalyst System for a Wacker-Type Oxidation Using TBHP as the Terminal Oxidant: Application to Classically Challenging Substrates; J. Am. Chem. Soc.; 2009; pp. 6076-6077; vol. 131, No. 17.

Sigman et al.; Ligand-Modulated Palladium-Catalyzed Aerobic Alcohol Oxidations; Accounts of Chemical Research; 2006; pp. 221-229; vol. 39 No. 3.
Zhang et al.; Palladium(II)-Catalyzed Enantioselective Aerobic Dialkoxylation of 2-Propenyl Phenols: A Pronounced Effect of Copper Additives on Enantioselectivity; J. Am. Chem. Soc. 2007; pp. 3076-3077; vol. 129, No. 11.
Mitsudome et al.; Convenient and Efficient Pd-Catalyzed Regioselective Oxyfunctionalization of Terminal Olefins by Using Molecular Oxygen as Sole Reoxidant; Angew. Chem. Int. Ed.; 2006; pp. 481-485; vol. 45.
Muzart; Aldehydes from Pd-Catalyzed Oxidation of Terminal Olefins; J. Muzart/Tetrahedron ; 2007; pp. 7505-7521; vol. 63.
Nishimura et al.; Palladium(II)-Catalyzed Oxidation of Terminal Alkenes to Methyl Ketones Using Molecular Oxygen; J. Chem. Soc., Perkin Trans.; 2000; pp. 1915-1918; vol. 1.
Malkov et al., On the Mechanism of Asymmetric Allylation of Aldehydes with Allytrichlorosilanes Catalyzed by QUINOX, a Chiral Isoquinoline N-Oxide; 2008; J. Am. Chem. Soc.; pp. 5341-5348; vol. 130.
Fox et al.; Bis-(2,5-diphenylphospholanes) with $sp^2$ Carbon Linkers: Synthesis and Application in Asymmetric Hydrogenation; J. Org. Chem.; 2008; pp. 775-784; vol. 73.

(Continued)

*Primary Examiner* — D M Seaman
(74) *Attorney, Agent, or Firm* — Thorpe North & Western LLP

(57) ABSTRACT

A quinoline-oxazoline compound having the formula:

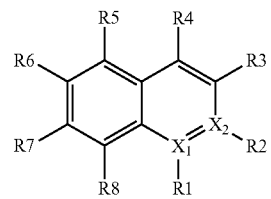

where one of $X_1$ and $X_2$ is N and the other is C and one of R1, R2 and R3 is Z wherein Z is an oxazoline radical having the formula

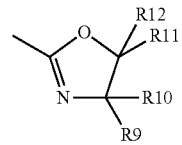

such that when $X_1$ is N R2 is Z and R1 is absent, and when $X_2$ is N either R1 or R3 is Z and R2 is absent. R1 and R3 through R12 are independently H or a pendant moiety which does not interfere with coordination of either N in the quinoline compound with a coordination center. These compounds can be complexed with a suitable coordination center such as catalytically active palladium and can be highly useful in catalytically oxidizing alkenes with high regioselectivity.

21 Claims, 2 Drawing Sheets

OTHER PUBLICATIONS

Malkov et al.; Quinox, a Quinoline-Type N-Oxide, as Organocatalyst in the Asymmetric Allylation of Aromatic Aldehydes with Allyltrichlorosilanes: The Role of Arene-Arene Interactions; Angew. Chem. Int. Ed.; 2003, pp. 3674-3677, vol. 42.

Machado et al., 2-(4,5-Dihydro-1,3-oxazol-2-yl)quinoline; ISSN 1600-5368 Acta Cryst.(2008) E64.

Poster; Expanding the Scope of the Wacker Oxidation: Oxidation of Protected Allylic Alcohols; Presented at ACS Annual Spring Meeting, Mar. 22, 2009 in Salt Lake City.

Sigman; BASF "Topics in Modern Chemistry"; Palladium-Catalyzed Oxidations for Organic Synthesis; Oct. 6, 2008.

* cited by examiner

QUINOLINE-OXAZOLINE COMPOUNDS AND THEIR USE IN OXIDATION SYNTHESIS

GOVERNMENT INTEREST

This invention was made with government support under Grant No. NIGMS RO1 GM63540 provided by NIH and Grant No. REU CHE-0649039 awarded by NSF. The United States government has certain rights to this invention.

BACKGROUND OF THE INVENTION

Conversion of alkenes to ketones can be conventionally accomplished by ozonolysis or by Tsuji-Wacker oxidation. Such conversion processes can be useful in a wide variety of industrial and synthetic chemistry applications as solvents, intermediates, or the like. In particular, Tsuji-Wacker oxidation, which is a palladium-catalyzed conversion of a terminal olefin to a methyl ketone, has widespread synthetic applications, owing to an extensive substrate scope and the orthogonal reactivity of olefins and ketones. However, a major limitation in the scope for Wacker oxidation chemistry is for allylic alcohols and their protected variants. Oxidation of theses substrates yields a high utility acyloin product, which is an attractive synthon for asymmetric synthesis. However, previous reports of Wacker oxidations on protected allylic alcohols using Tsuji-type conditions found diminished selectivity for the desired methyl ketone and frequently yielded 1:1 formation of the corresponding aldehyde.

The current approach to accessing the methyl ketone products from allylic alcohols is a two-step procedure, which generally utilizes stoichiometric amounts of mercury, palladium, and copper. Although this method allows for access to acyloin products in good yields, the method also results in high metal loadings and toxic byproducts. Therefore, existing techniques have limitations which reduce their desirability in commercial use.

SUMMARY OF THE INVENTION

In light of the problems and deficiencies note above, the present invention provides a quinoline compound having the formula:

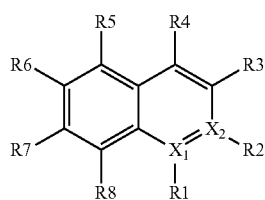

where one of $X_1$ and $X_2$ is N and the other is C and one of R1, R2 and R3 is Z wherein Z is an oxazoline radical having the formula

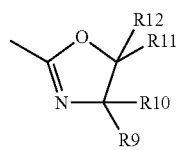

such that when $X_1$ is N R2 is Z and R1 is absent, and when $X_2$ is N either R1 or R3 is Z and R2 is absent. R1 and R3 through R12 are independently H or a pendant moiety which does not interfere with coordination of either N in the quinoline compound with a coordination center.

These compounds can be complexed with a suitable coordination center such as catalytically active palladium. Furthermore, the quinoline catalyst complex can be highly useful in catalytically oxidizing alkenes. Typically, the alkene is exposed to the quinoline catalyst complex in the presence of a mediation compound to form a ketone.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

The present invention will become more fully apparent from the following description and appended claims, taken in conjunction with the accompanying drawings. Understanding that these drawings merely depict exemplary embodiments of the present invention and they are, therefore, not to be considered limiting of its scope.

DETAILED DESCRIPTION OF EXEMPLARY EMBODIMENTS

Figure 1:
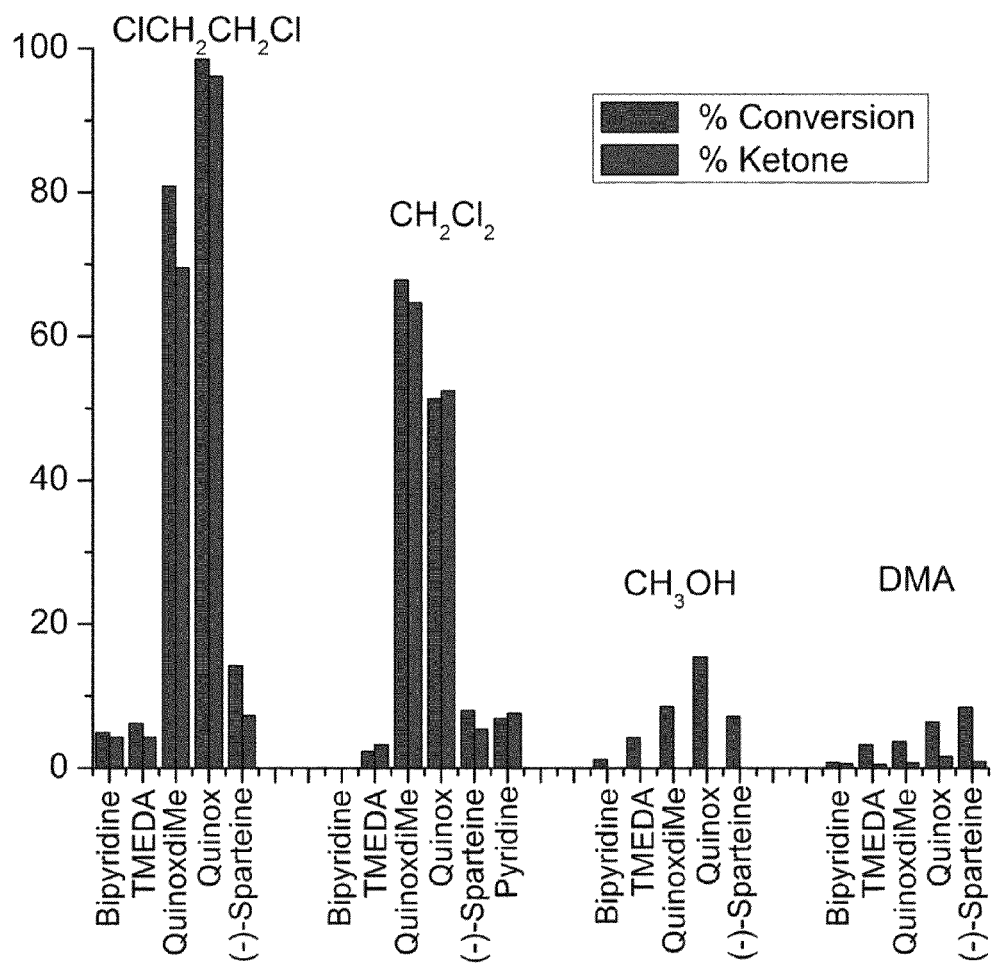
FIG. 1 is a graph of conversion and yield for several ligand-solvent systems comparing conventional ligands with two quinoline ligands in accordance with one embodiment of the present invention.

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

DEFINITIONS

In describing and claiming the present invention, the following terminology will be used.

The singular forms "a," "an," and "the" include plural referents unless the context clearly dictates otherwise. Thus, for example, reference to "a moiety" includes reference to one or more of such groups and reference to "exposing" refers to one or more such steps.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "aryl" refers to aromaticity of compounds which can be carbocyclic or heterocyclic, including single and multiple ring systems.

As used herein, "derivatives" of side groups are intended to cover substituted groups where one or more hydrogens is replaced by a corresponding side group. The replacement side groups can be exemplified generally by alkyls, aryls, alkoxy, non-aromatic cyclics, silyls, amino, and the like. As long as functionality of the compound is maintained no particular limitation on the specific nature of the derivative is intended.

As used herein, "ketone" refers to a carbonyl bonded to two carbon atoms. As such ketones also include acyloins. For example, protected allylic alcohols can be converted to acyloin ketones in accordance with the present invention.

As used herein, a plurality of compositional elements and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

In the present disclosure, any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Embodiments of the Invention

A class of quinoline-oxazoline compounds is disclosed. In particular, a quinoline compound can have the general formula:

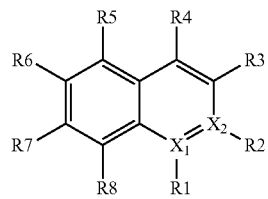

(I)

where one of $X_1$ and $X_2$ is N and the other is C and one of R1, R2 and R3 is Z wherein Z is an oxazoline radical having the formula

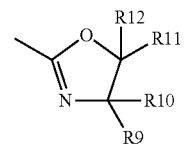

(II)

such that when $X_1$ is N R2 is Z and R1 is absent, and when $X_2$ is N either R1 or R3 is Z and R2 is absent. As such, the oxazoline moiety is bonded to a carbon which is adjacent the nitrogen of the quinoline core. As discussed and illustrated more below, this orientation allows the nitrogen of the oxazoline and the nitrogen of the quinoline to form a bidentate ligand capable of complexing with a coordination center. Side groups R1 and R3 through R12 can be a wide variety of moieties which are not particularly limited as long as the side groups do not interfere in complexing with the coordination center. Accordingly, R1 and R3 through R12 can each independently be H or a pendant moiety which does not interfere with coordination of either N in the quinoline compound with a coordination center. The quinoline compounds can be either chiral or achiral. Chiral quinoline compounds offer the ability to form corresponding chiral ketone products.

Although R1 and R3 through R12 can be a wide variety of side groups, the following are representative of suitable moieties for these positions. Non-limiting examples of suitable side group classes include hydrogen, alkyls, alkyloxys, aryls, halides, cyclics (including heterocyclics), carbonyls, aminos, silyls, derivatives thereof, and combinations thereof (e.g. alkaryl, arylakyl, alkoxy aryl, alkyl heterocyclic, etc). Alkyls can be straight or branched and can include substituted groups such as halides (including fluorine, chlorine and bromine), acids (including protected acids, carboxylic acids, sulfonic acids, etc), alkyloxy side chains, and the like. In one aspect, the alkyls can be lower alkyls having fewer than 10 carbons, and in some aspects fewer than 8 carbons. Non-limiting examples of lower alkyls can include methyl, ethyl, propyl, t-butyl, n-butyl, isopropyl, isobutyl, sec-butyl, adamantyl. Alkyloxy side groups can include, but are not limited to, methoxy, ethoxy, propoxy, substituted versions of these and polyalkyloxy. Aromatic side groups can generally include aryls which are carbocyclic or heterocyclic aromatic, and the like. Non-limiting examples of suitable aryl radicals can include phenyl, phenoxy, napthyl, and substituted derivatives thereof (e.g. methyl, lower alkyl, halide, etc.). Aryls can also include radicals of heterocyclic aromatics such as pyridine, indols, oxetanes, thietanes, furans, pyrrols, oxazoline (in addition to the primary oxazoline), thiazoles, imidazoles, thiolanes, triazoles, pyrans, pyridines, thiazines, piperazines, purines, triazines, derivatives thereof, and the like. In one aspect, R1 and R3 through R12 are each hydrogen. In another aspect, at least one of R1 and R3 through R12 is methyl. In another specific aspect, R9 and R10 are methyl.

Several example sub-classes of the above quinoline compounds are illustrated below as: quino line-2-oxazolines, 1-isoquinolineoxazolines, and 3-isoquinolineoxazoline. Each of these sub-classes can utilize a choice of side groups as identified above with respect to the general formula. In one aspect, the quinoline compound is a quinoline-2-oxazoline having the formula:

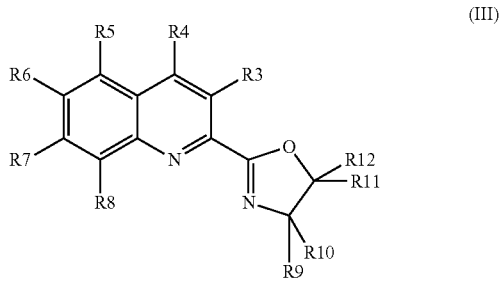

(III)

In this case, R1 is absent and R2 is Z (Formula II). In one alternative, R3 through R12 are all hydrogen. In another similar alternative, R3 through R8, R11 and R12 are hydrogen and R9 and R10 are methyl (e.g. quinoline-2-3,3-dimethyl oxazoline).

In another aspect, the quinoline compound is a 1-isoquinolineoxazoline having the formula:

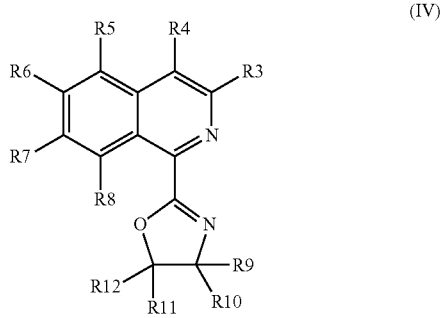

(IV)

In this case, R1 is Z (Formula II) and R2 is absent. Each of R3 through R12 can be chosen from those side groups previously discussed. In one specific aspect, R3 through R12 are each hydrogen.

Another class of quinoline compounds that are particularly useful include 3-isoquinolineoxazolines having the formula:

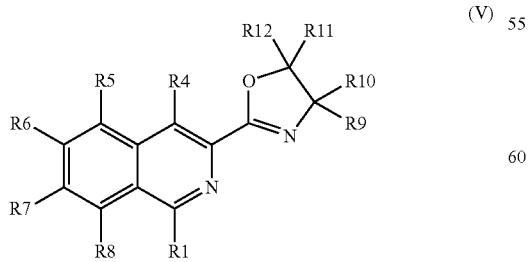

(V)

In this case, R2 is absent and R3 is Z (Formula II). In one aspect, each of R1 and R4 through R12 are hydrogen.

Regardless of whether the oxazoline group (Formula II) is oriented at R1, R2 or R3 positions, the arrangement of the nitrogen in the quinoline core and the nitrogen of the oxazoline is substantially them same. In particular, the nitrogens are separated by three bonds (two atoms) such that a bidentate coordinating ligand is formed of the quinoline-oxazoline compound. Although the quinoline compound can be formed alone or in the absence of a corresponding complimentary coordination center, typically a complexed quinoline compound can be provided. The coordination center can most often be a catalytically active metal although other organic or inorganic coordination centers can also be suitable. Non-limiting examples of suitable coordination metals can include palladium (especially $Pd^{2+}$), Pt, Rh and Ni.

The quinoline oxazoline compounds can be readily synthesized in a two step process. First, a starting quinoline core of quinaldic acid can be functionalized by reaction with an ethanolamine to form a quinoline carboxamide. Second, the carboxamide can be converted to an oxazoline via reaction of the alcohol to form a suitable leaving group. The various functional groups R1 through R12 can be present in the starting quinoline and/or ethanolamine or can be added subsequently via metallation, deprotonation, nucleophilic substitution reactions, or the like. A specific example for producing quinoline-2-oxazolines can follow the following reaction scheme:

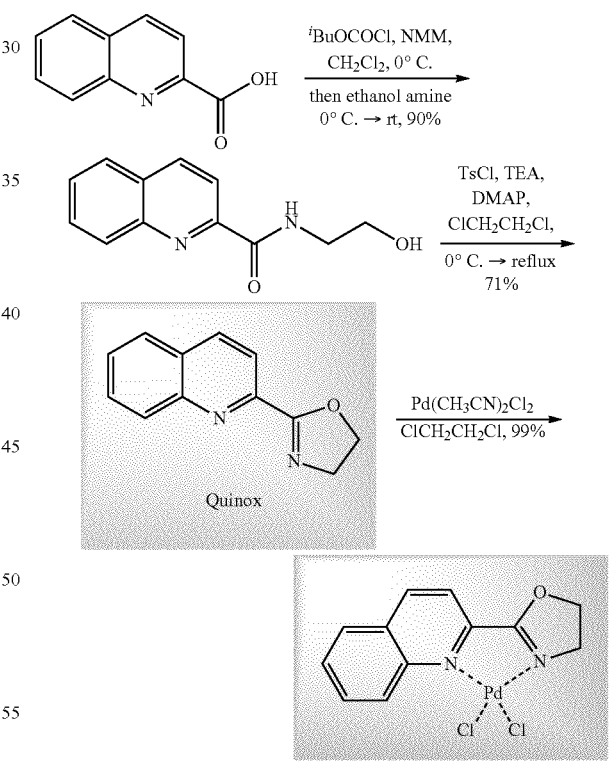

The quinoline oxazoline compounds of the present invention can be particularly suitable for use in catalytically oxidizing an alkene to form a ketone. Ketones can be useful in a wide variety of industrial and synthetic chemistry applications. Non-limiting examples of uses of ketones can include nucleophilic addition reactions to form alcohols, geminal diols, imines, hydroxyalkynes, ketals, thioacetals, hydrazones, and the like. A number of reaction schemes for ketones are also well known such as Haller-Bauer reaction, Wittig reaction, Norrish reaction, Haloform reaction, Robinson-Gabriel synthesis, Willgerodt reaction, and the like. Ketones are also useful as solvents and in forming pharmaceuticals. Generally, an alkene can be exposed to a quinoline catalyst complex in the presence of a mediation compound to form the ketone. The quinoline catalyst complex is a complex of the coordination center and quinoline compound previously discussed.

A wide variety of alkenes can be oxidized using the quinoline catalyst complex. These alkenes can be terminal alkenes or internal alkenes as long as the alkene functionality is accessible to the complex and mediation compound. For example, when the alkene is a terminal alkene the ketone is a methyl ketone. Without being bound to any particular theory, the overall reaction mechanism for such terminal alkenes may be described as follows using t-butyl hydroperoxide as the mediation compound (and keto-oxygen source) and palladium as the coordination center:

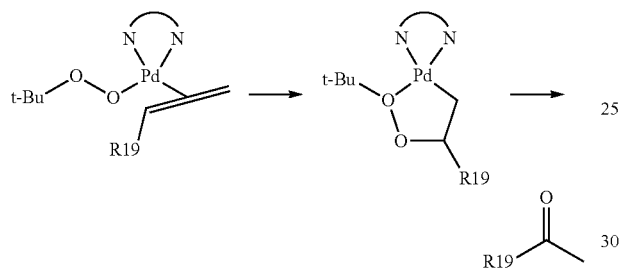

where R19 is a carbon-containing functional group. In this proposed pathway, a coordinatively saturated species is formed between the mediating peroxide, the quinoline ligand, and the alkene. This peroxide mediated oxidation also allows a strong preference for oxidation at the Markovnikov position as opposed to the anti-Markovnikov position which leads to the undesirable corresponding aldehyde, especially in the case of protected allylic alcohols (when R19 includes a protected alcohol at the first carbon). Also protected allylic amines are suitable functionalities at the first carbon.

The carbon-containing functional group of the alkene is not particularly limited as long as such group does not interfere with oxidation of the alkene to a ketone via the quinoline catalyst complex. Suitable carbon-containing functional groups can include alkyls, aryls, cyclic, amino, sulfo, silyl, and derivatives or combinations thereof. Non-limiting examples of alkyls can include C1 to C20 linear or branched alkyls. Alkyls can be substituted with a variety of side groups such as, but not limited to, halogens, alcohols, amines, acetals, ketals, dithianes, and combinations thereof. Non-limiting examples of suitable aryls can include phenyl, napthyl, furyl, pyridyl and aromatic heterocyclics. In one specific aspect, the terminal alkene can be a non-aromatic alkyl such as 6-(2,2-dimethyl-1,3-dioxolane)-hex-1-ene having the formula

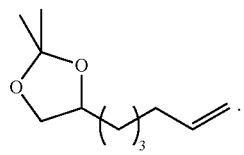

Examples of suitable terminal alkenes include styrenes such as, but not limited to, 1-methyl-4-vinyl benzene (4-methylstyrene)

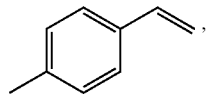

t-butyl-4-vinylphenylcarbamate

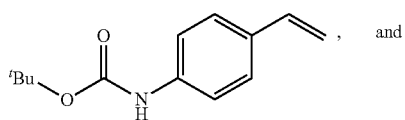, and 1-nitro-3-vinyl benzene (3-nitrostyrene)

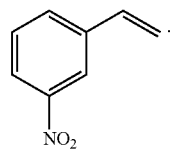

In another alternative aspect, the terminal alkene can be a protected allylic alcohol having the formula

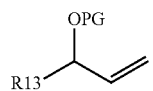

where PG is a protecting group and R13 is carbon-containing functional group. Unlike conventional oxidation catalysts which tend to produce substantial amounts of aldehydes along with the desired ketones, the ketones formed in this aspect are acyloin products with substantially reduced or eliminated aldehyde formation. The carbon-containing functional group R13 can be chosen generally from groups identified suitable for R19 and R3 through R12. In one specific aspect, R13 can be pentyl, phenyl, cyclohexyl, octyl, nonanol, methyl nonanoate, chlorononyl, 4-methyl phenyl, 4-BOCN-HPh, 3-NO₂Ph (nitrophenyl), and the like.

The protecting group PG can be any suitable group which bonds to the oxygen during oxidation, and which can be removed subsequent to oxidation of the alkene functional group. Non-limiting examples of suitable PG moieties include acetals, esters, silyl ethers, alkoxyalkyl ethers, and the like. Specific non-limiting examples of suitable PG moieties include acetate, benzoyl, pivaloyl, tert-butyldimethylsilyl, methoxymethyl ether, ethoxymethyl ether, ethoxyethyl ether, benzyl, para-methoxybenzyl, dimethoxytrityl, methoxytrityl, trityl, methylthiomethyl ether, β-methoxyethoxymethyl ether, trimethylsilyl ether, triisopropylsilyl, and tetrahydropyranyl. In one aspect, the protected non-aromatic cyclic protected allylic alcohol can be 1-cyclohexylallyl acetate having the formula

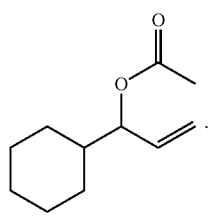

The quinoline catalyst complexes of the present invention are particularly versatile and can also be used to convert internal alkenes to corresponding ketones. Internal alkenes generally can have the formula

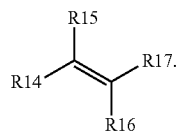

Internal alkenes which include a protected alcohol can have the formula

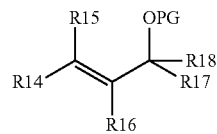

where PG is a protecting group, R14 is a carbon-containing functional group and R15 through R18 are hydrogen or a carbon-containing functional group. These R14 through R18 can be chosen from among those moieties previously discussed for R19 and R3 through R12. Generally, R14 can be lower alkyl, aryl, alkaryl, aryalkyl, alkoxy, non-aromatic cyclic (including heterocyclic), aromatic (including heterocyclic), and derivatives thereof.

In yet another alternative aspect, the quinoline catalyst complexes can be used for oxidation of protected amines having either a terminal or internal alkene functionality. Such protected amines have the general formula

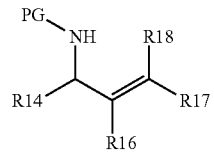

where PG is selected as previously described and R14 and R16 through R18 can be hydrogen or side groups as previously discussed.

The quinoline catalyst complexes can also exhibit high regioselectivity, depending on the choice of components. High regioselectivity can be influenced by choosing substrates which are tailored to allow preferential oxidation at one end of the alkene functionality. For example, side groups can be chosen so as to provide steric hindrance to prevent or reduce access of the complex to one end of the alkene functionality while allowing access to the other end. For example, given the following general alkene substrate structure, one of R20 and R21 or R22 and R23 can be hydrogen while the others are a blocking group (e.g. carbon-containing group, amino, silyl, etc.) or groups such as those previously discussed (e.g. protected alcohols, carbon-containing groups, and the like).

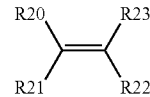

Thus, the hydrogen bonded alkenyl carbon becomes the oxidation site which reacts with the quinoline catalyst complex.

The quinoline catalyst complexes can also be asymmetric catalysts which can be useful when enantiomeric products are desired. Further, a racemic mixture of starting alkenes can be enantiomerically enriched through preferential oxidation of one enantiomer over the other (e.g. a result of chirality of the complex).

Although the above protected allylic alcohols are shown with the alcohol functionality adjacent the alkene functionality, this is not required. For example, protected alcohols can be two or more carbon atoms separated from the double bond. One non-limiting example of such a protected aromatic allylic alcohol includes tert-butyldimethyl(1-phenylbut-3-enyloxy)silane having the formula

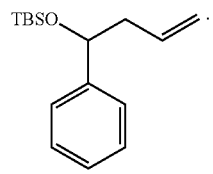

As with the terminal alkenes, the protecting group PG can generally be acetals, esters, silyl ethers, alkoxyalkyl ethers, or combination thereof. In one specific aspect, the internal alkene is

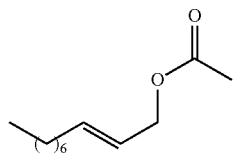

e.g. where PG is acetyl, R17, R18 and R15 are hydrogen, and R14 is heptyl. In this case, a 5 mol % of Pd(quinox)Cl$_2$, 12 mol % AgSbF6 and 12 equivalents of TBHP in DCM as solvent at 0.1 M starting at room temperature yielded 95% of the corresponding ketone (i.e. β-acetoxy ketone).

The mediation compound can be any suitable oxygen source which is compatible with the quinoline catalyst complex. Most often the mediation compound is an oxidant such as a peroxide, although other oxidants may be suitable e.g. ozone, hypochlorites, chlorate, nitric acid, chromium oxides, manganates, and the like. Suitable peroxides can include, but are not limited to, an alkyl peroxide, hydrogen peroxide, and mixtures thereof. In one aspect, the peroxide is t-butyl hydroperoxide. The t-butyl hydroperoxide can be present in excess from about 2 eq. to about 50 eq, and in one aspect from 6 eq. to about 20 eq., and one another aspect about 6 eq. to about 12 eq.

A non-complexing and non-coordinating counterion can also be included during oxidation of the corresponding alkene. The counterion primarily provides charge balance to the complex and associated reaction intermediates. Silver compounds of a suitable counterion can be particularly useful since the corresponding salt (AgCl) is insoluble in most solvents such that precipitation occurs and the counterion is substantially completely available. Non-limiting examples of suitable counterion salts can include $AgSbF_6$, $AgBF_4$, $AgPF_6$, $AgF_3C_2O_2$, silver tetrakis(fluoroaryl)borate (BArF), and combinations thereof.

The above oxidation reactions can also be performed in the presence of an optional solvent for the alkene substrate. Depending on the particular choice of components, the solvent can also substantially affect conversion and yield of the alkene to a ketone. It is thought that well performing solvents also do not coordinate with the dicationic complexes. Non-limiting examples of suitable solvents can include $CH_2Cl_2$, 1,2-dichloroethane, t-butylmethylether, and mixtures thereof although others can be used. In one aspect, the solvent can be $CH_2Cl_2$. In another aspect, the solvent can be 1,2-dichloroethane.

EXAMPLES

General Considerations

Dichloromethane (DCM), 1,2-dichloroethane (DCE), and triethylamine (TEA) were distilled from $CaH_2$ for ligand and substrate synthesis. Unless otherwise noted all chemicals were purchased from Aldrich or Acros and used without further purification. Acetic anhydride was purchased from Mallinckrodt and used without further purification. All silver salts were stored in a nitrogen filled glove box and protected from light. (S)-1-octen-3-ol was purchased from Fluka and used without further purification. Quinaldic acid and 1-isoquinaldic acid were purchased from AK scientific and used without further purification. 4-N,N-dimethylaminopyridine (DMAP) was recrystallized from toluene and Tosylchloride (TsCl) was recrystallized from chloroform and petroleum ether prior to use. Ethanolamine was fractionally distilled immediately prior to use. 4-Methyl styrene and m-Nitro styrene were passed through a plug of activated alumina immediately prior to use.

Analytical thin layer chromatography was performed with Whatman K6F Silica 60 Å plates. Flash Chromatography was performed using Dynamic Adsorbents Inc. flash silica gel 32-63 um. All NMR spectra were obtained on one of the following instruments: Inova 500 MHz (TRIAX probe), Varian 500 MHz, or Unity 300 MHz and referenced to the residual solvent peak from $CHCl_3$ at 7.27 ppm. All melting points are uncorrected and recorded on a Thomas Hoover Unimelt capillary melting point apparatus. Elemental Analysis was obtained through Columbia Analytical Services. FT-IR spectra were obtained on a Thermo Nicolet 380 FT-IR. HRMS were obtained with either an ESI or APCI source on a Waters LCT Premier XE. GC conversions were determined relative to an internal standard. Although no problems occurred during performance of these examples, highly concentrated solutions of TBHP in the presence of transition metals can be dangerous and care should be taken when repeating these procedures.

Comparison of Quinoline Complexes with Several Conventional Bidentate Complexes

Several conventional bidentate amine ligands were evaluated in various solvents. These ligands included bipyridine, phenanthroline, bathocuprione, TMEDA, diimine, (−)-sparteine, and two quinoline compounds as shown below.

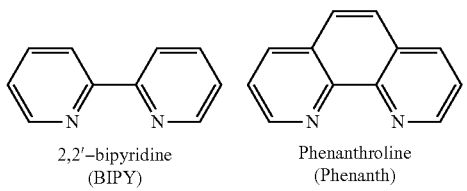

2,2′-bipyridine (BIPY)

Phenanthroline (Phenanth)

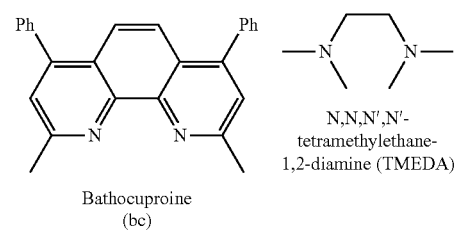

Bathocuproine (bc)

N,N,N′,N′-tetramethylethane-1,2-diamine (TMEDA)

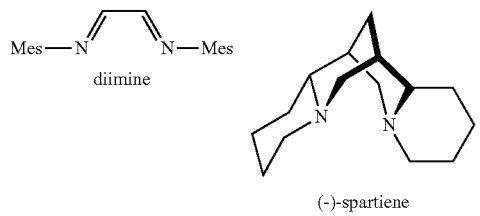

diimine (−)-spartiene

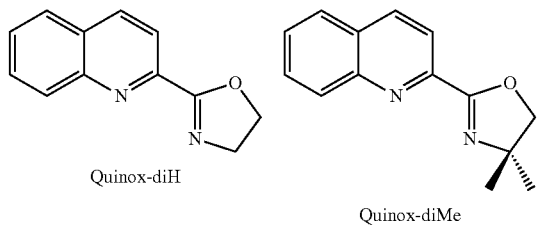

Quinox-diH

Quinox-diMe

Pyridine was also evaluated as a potential ligand in $CH_2Cl_2$. The tested solvents included $CH_2Cl_2$, $CH_3OH$, 1,2-dichloroethane, and DMA.

Standard solutions of 1-octen-3-yl acetate were made so that 240 μL of the respective solvent (DCE, DCM, Methanol, or DMA) would deliver 0.1 mmol along with ~10 wt % of dodecane as an internal standard. Standard solutions were also made of ligands which were viscous or that 0.006 mmol would be too small to accurately weigh. A standard solution of $Pd(CH_3CN)_2Cl_2$ was made so that 0.005 mmol would be added to each vial. To each 2 mL brown glass reaction vial was weighed $AgBF_4$ (2.3 mg, 0.012 mmol) in the dark and ligand (0.006 mmol, if standard solution then added as a specific volume). To vials with ligand weighed directly into them was added solvent of the same amount as was used for ligand standard solutions. A micro stir bar was added to each vial and the mixture was stirred. A specified amount of the $Pd(CH_3CN)_2Cl_2$ standard solution was added to each vial. The mixture was stirred for ~10 min before 70 wt % $TBHP_{(aq)}$ (1.5 mmol, 215 μL) was added to each vial. Finally the substrate was added to the vials as a specified volume, which brought the reaction mixtures to 0.1M. The reactions proceed according to the general formula

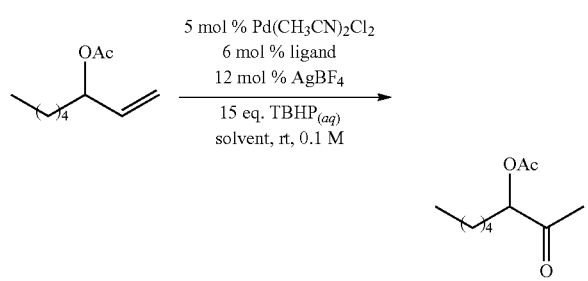

Aliquots (~50 µL) of the reaction mixture were taken periodically, passed through a small silica pipette with ethyl acetate, and analyzed for conversion and product formation by gas chromatography. The conversions and products were calculated relative to the dodecane internal standard. Pyridine was also evaluated as a ligand in DCM at 12 mol % relative to Pd(CH$_3$CN)$_2$Cl$_2$. The conversion and yield results for each substrate and solvent tests is shown in FIG. 1.

Of the ligands evaluated, only reactions using the quinoline-2-oxazoline (Quinox) framework showed significant product formation. It is also noted that CH$_2$Cl$_2$ as the solvent is particularly well suited to this particular combination of components.

Counter Ion Screen:

The silver salts of the counter ions evaluated, of the form Ag$^+$ X$^-$ (0.012 mmol) (except BARF$^-$ which was in the form of the sodium salt) included BF$_4^-$, TfO$^-$, TsO$^-$, SbF$_6^-$, BARF$^-$, and PF$_6^-$. The sodium salt of BARF- has the formula

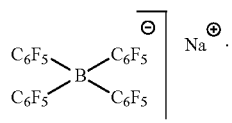

Figure 2:
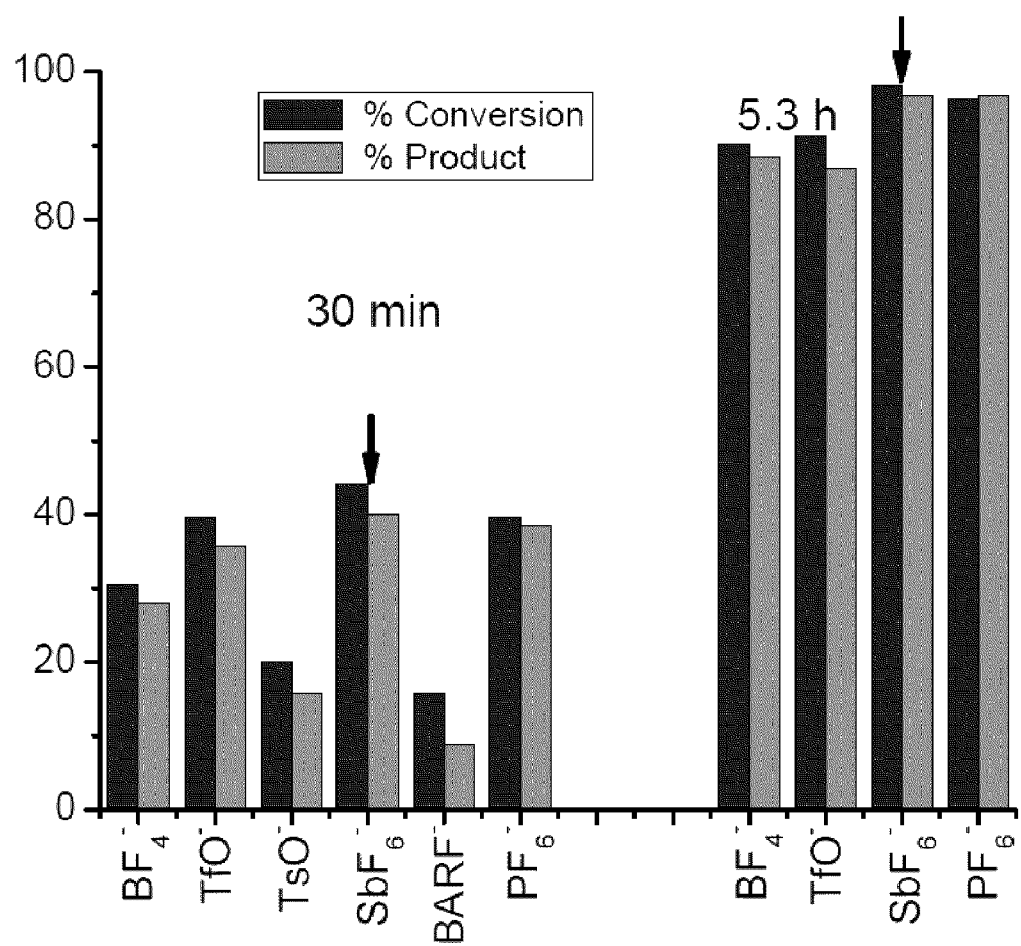
FIG. 2 is a graph shows conversion and yield as a function of counterion in accordance with one embodiment of the present invention.

Each of the salts were weighed into 2 mL brown vials followed by a standard solution made so that quinox ligand (0.001 mmol) and Pd(quinox)Cl$_2$ (0.005 mmol) were added in a specified volume of solution. The mixtures were stirred for ~10 min, before 70 wt % TBHP$_{(aq)}$ (1.3 mmol, 186 µL) was added to the vials. A standard solution was made so a specified volume would add substrate (0.1 mmol) and ~10 wt % dodecane as an internal standard to the vials and bring the reaction mixture to 0.1 M. Alliquots (~50 µL) of the reaction mixture were taken periodically, run through a small silica pipette with ethyl acetate, and analyzed for conversion and product formation by gas chromatography. Results are shown in FIG. 2.

It was found that the less coordinating SbF$_6^-$ counterion led to the most rapid and selective conversion of olefin. PF$_6^-$ was nearly as good, however had slightly less selectivity for methyl ketone formation and is more expensive than SbF$_6^-$. OTf$^-$ and BF$_4^-$ counterions led to a slower reaction, although good selectivity was still observed. Selectivity was measured as % product/% conversion.

Synthesis of Quinox diH Ligands

To an oven dried 250 mL round bottomed flask was weighed quinaldic acid (1.734 g, 10.0 mmol). A magnetic stir bar was added and the flask was put under N2 atmosphere. The flask was charged with DCM (100 mL) and cooled to 0° C. in an ice bath. The flask was then charged with N-methyl morpholine (1.44 mL, 15.0 mmol) and isobutlychloroformate (1.51 mL, 11.5 mmol) via syringe addition. The reaction was allowed to stir at 0° C. for 20 min until the solution became cloudy. At which point freshly distilled ethanolamine (695 uL, 11.5 mmol) was added slowly to the flask via syringe. The reaction mixture was allowed to slowly warm to room temperature to form N-(2-hydroxyethyl)quinoline-2-carboxamide was formed according to the formula

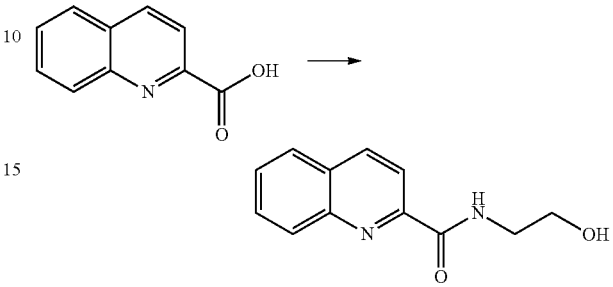

The reaction mixture was quenched, after stirring for 2 h at room temperature, with saturated sodium bicarbonate solution (80 mL) and transferred to a reparatory funnel with DCM (2×15 mL). The layers were separated, and the aqueous layer was back extracted with DCM (2×30 mL). The combined organic phases were washed with water (1×70 mL), which was back extracted with DCM (2×25 mL). The combined organic phases were washed with brine (1×100 mL), which was back extracted with DCM (1×25 mL). Combined organic phases were dried over sodium sulfate, filtered and concentrated under reduced pressure. The resulting mixture was purified by flash chromatography using a mixed solvent system: 70% EtOAc, 19% DCM, 10% Hexanes, and 1% MeOH. The product was isolated (1.95 g, 90% yield) as a colorless solid by recrystallizing by slow evaporation of DCM. The product was confirmed via NMR, IR and HRMS analyses. Measured melting point was 107-109° C.

Quinoline-2-oxazoline

N-(2-hydroxyethyl)quinoline-2-carboxamide was dissolved in DCE (40 mL) in an oven dried 100 mL pear bottomed flask. To a 250 mL 3 necked round bottomed flask was fitted a water condenser, and a magnetic stir bar was added. p-Toluene sulfonyl chloride (2.2288 g, 11.65 mmol) and N,N-dimethylaminopyridine (95.4 mg, 0.78 mmol) were added to the reaction flask. The flask was placed under N$_2$ atmosphere. DCE (30 mL) was added to the reaction flask and cooled to −5° C. The reaction flask was charged with triethylamine (5.50 mL, 39 mmol). The reaction mixture was stirred for 10 min and allowed react according to the formula

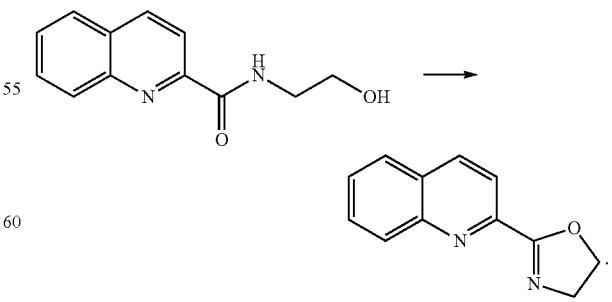

The solution of amide in DCE was slowly cannulated into the reaction vessel over the course of 20 min. The pear bottomed flask was rinsed with DCE (15 mL), which was also cannulated to the reaction mixture. The reaction mixture was stirred at −5° C. for 5 min and then allowed to slowly warm to room temperature. The reaction was monitored by TLC until all of the amide had been consumed, which took ~2 h. The reaction mixture was then heated to reflux in an 85° C. oil bath for 3 h. The reaction mixture was then cooled to room temperature and quenched with saturated sodium bicarbonate solution (80 mL). The mixture was transferred to a reparatory funnel, diluted with DCM (120 mL) and saturated sodium bicarbonate (70 mL). The layers were separated and the aqueous layer was back extracted with DCM (50 mL). The combined organic phases were washed with water (2×100 mL), which were each back extracted with DCM (50 mL). The combined organic phases were washed with brine (1×150 mL), and then dried over sodium sulfate, filtered and concentrated under reduced pressure. The resulting mixture was purified by flash chromatography using 2% methanol in DCM. The product was isolated as a white solid (1.10 g, 71% yield) and had a melting point of 109-110° C.

Pd(quinox)Cl$_2$:

Quinoline-2-oxazoline (695.6 mg, 3.51 mmol) was weighed into an oven dried 100 mL round bottomed flask. A magnetic stir bar was added and the reaction was placed under N$_2$ atmosphere. DCE (30 mL) was added to the reaction flask and stirred until quinox was completely dissolved. Pd(CH$_3$CN)$_2$Cl$_2$ (880.3 mg, 3.39 mmol) was added to the reaction flask. The reaction mixture was allowed to stir for 16 h to form quinoline-2-oxazoline according to the reaction

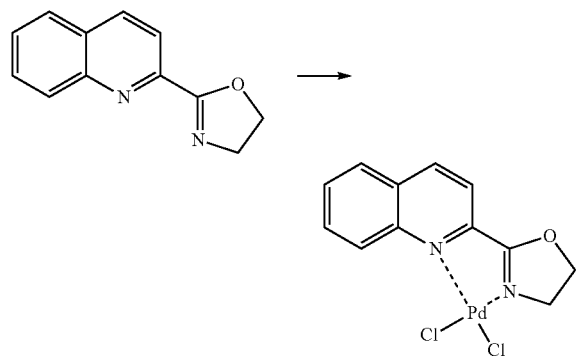

A precipitate formed and was filtered off using a Buchner funnel. The Pd(quinox)Cl$_2$ complex was isolated (1.24 g, 99% yield) as an orange powder. Pd(quinox)Cl$_2$ is completely insoluble in all common NMR solvents and the reaction becomes homogeneous upon treatment with aqueous TBHP. A decomposition temperature of 285° C. was measured.

Synthesis of Quinox diMe ligand

To an oven dried 250 mL round bottomed flask was weighed quinaldic acid (866 mg, 5.0 mmol). A magnetic stir bar was added and the flask was put under N2 atmosphere. The flask was charged with DCM (50 mL) and cooled to 0° C. in an ice bath. The flask was charged with N-methyl morpholine (720 μL, 7.5 mmol) and isobutlychloroformate (752 μL, 5.75 mmol) via syringe addition. The reaction was allowed to stir at 0° C. for 10 min until the solution became cloudy. At which point 2-methyl-2-aminopropanol (550 uL, 5.75 mmol) was added slowly to the flask via syringe. The reaction mixture was allowed to slowly warm to room temperature. The reaction was quenched after 2 h with 1M HCl solution (30 mL) and transferred to a separatory funnel with DCM (50 mL). The layers were partitioned and the organic phase was washed with H2O (2×30 mL) and brine (1×40 mL). After drying over Na$_2$SO$_4$ and filtration, the mixture was concentrated under reduced pressure. The crude mixture was purified by flash chromatography eluting with a 1:1 mixture of EtOAc and hexanes to afford N-(1-hydroxy-2-methylpropan-2-yl)quinoline-2-carboxamide as a colorless oil in 91% yield (1.112 g, 4.55 mmol) according to the following reaction

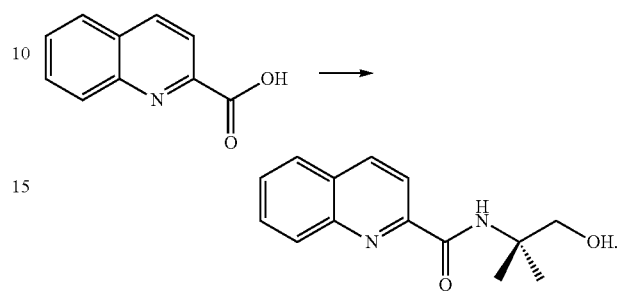

To an oven dried 250 mL round bottomed flask was weighed p-Toluene sulfonyl chloride (1.049 g, 5.5 mmol) and N,N-dimethylaminopyridine (39.1 mg, 0.32 mmol). A magnetic stirbar was added and the flask was placed under N2 atmosphere. The flask was charged with DCE (20 mL) and triethylamine (3.2 mL, 23 mmol). The N-(1-hydroxy-2-methylpropan-2-yl)quinoline-2-carboxamide (1.112 g, 4.55 mmol) was dissolved in DCE (15 mL) and added to the flask dropwise via syringe. The reaction mixture was stirred at 0° C. for 15 min, before a reflux condenser was fitted to the flask and heated to reflux for 16 h. The reaction mixture was cooled to room temperature, transferred to a separatory funnel and diluted with DCM (70 mL). The organic phase was washed with saturated NaHCO$_3$ solution (2×70 mL), H$_2$O (2×70 mL), and Brine (1×70 mL). Dried over Na$_2$SO$_4$, filtered and concentrated under reduced pressure. The crude mixture was purified by flash chromatography eluting with 20%→30% acetone in hexanes to afford 4,4-dimethyl-2-(quinoline-2-yl)-oxazoline in 47% yield (484 mg, 2.14 mmol) according to the reaction

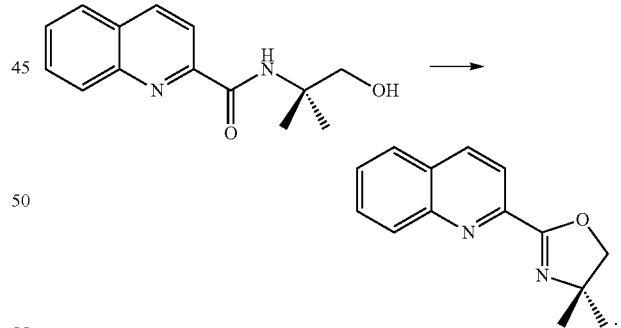

Preparation of Substrates:

Oct-1-en-3-yl acetate, tert-butyldimethyl(oct-1-en-3-yloxy)silane, 4-(tert-butyldimethylsiloxy)-4-phenylbutan-2-one, 10-undecenoic acid methyl ester, 4-hex-5-enyl-2,2-dimethyl-[1,3]dioxolane, 11-choroundec-1-ene, and tert-butyl 4-vinylphenylcarbamate were prepared following literature procedures and purity confirmed via $^1$H NMR. Adamantyl ethylene was prepared following the literature procedure and purity was confirmed by $^1$H NMR. Enantiomerically enriched oct-1-en-3-yl acetate was prepared from the purchased enantiomerically enriched alcohol and was protected by the same procedure as the racemate. Retention of enantiomeric excess was confirmed by chiral phase column gas chromatography. Enantiomerically enriched 1-phenylbut-3-en-1-ol was synthesized using the literature method and enantiomeric excess was confirmed using an HPLC method.

3-(ethoxymethoxy)oct-1-ene:

To a flame dried 250 mL round bottomed flask containing a stirbar and under N2 atmosphere, was combined 1-octen-3-ol (3.08 mL, 20 mmol), DIPEA (84 mL, 40 mmol), and DCM (40 mL). Next (chloromethoxy)ethane (2.23 mL, 24 mmol) was added via syringe. The reaction mixture was heated to reflux for 12 h and then cooled to room temperature. The protected allylic alcohol was thus formed according to the reaction

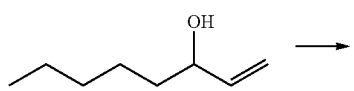

TLC indicated complete consumption of the starting material, and the reaction was quenched with saturated aqueous Na$_2$SO$_4$ solution (50 mL). The reaction mixture was transferred to a separatory funnel with ether. The phases were partitioned and the organic layer was washed with brine. The aqueous layer was back-extracted with DCM. The combined organic layers were dried over Na$_2$SO$_4$, filtered and concentrated under reduced pressure. The resulting mixture was purified by flash chromatography using 2.5% ether in hexanes to give 3-(ethoxymethoxy)oct-1-ene as a colorless oil (3.5 g, 95% yield).

General TBHP Mediated Wacker Reaction:

Table 1 reports individual examples while the following description provides a common reaction scheme used in each example with deviations noted. In the dark, AgSbF$_6$ (51.5 mg, 0.15 mmol), Pd(quinox)Cl$_2$ complex (22.5 mg, 0.06 mmol), and a magnetic stir bar were added to a 100 mL round bottomed flask. DCM (4.8 mL) was added to the flask and the mixture was stirred for 15 min. The mixture was then diluted with DCM (20 mL) and 70 wt % TBHP$_{(aq)}$ (5.2 mL, 36 mmol) was added. The resulting mixture was stirred for an additional 10 min, before being cooled in an ice bath. Once the solution had cooled, the substrate (3.0 mmol) was added with stirring. After 5 min, the ice bath was removed and the reaction mixture was allowed to slowly warm to room temperature. Once TLC indicated complete consumption of starting material, the reaction was quenched with a saturated aqueous solution of Na$_2$SO$_3$ (50 mL) to consume excess TBHP. The mixture was transferred to a separatory funnel and diluted with hexanes (50 mL). The aqueous layer was separated and back extracted with hexanes (25 mL). The combined organics were washed with water (4×25 mL) and brine (50 mL). The combined organic phases were dried over MgSO$_4$, filtered and concentrated under reduced pressure. The crude material was purified by silica gel flash chromatography if necessary; the product containing fractions were combined and concentrated under reduced pressure. The general reaction scheme was as follows:

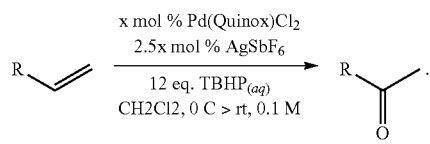

TABLE 1

| Entry | Substrate | x | % Yield[a] | Time |
|---|---|---|---|---|
| | OPG⁄⁄₄ | | | |
| 1[b] | PG = Ac | 5 | 89 | 20 h |
| 2[c] | PG = TBS | 2 | 77 | 4.5 h |
| 3[d] | PG = CH$_2$OCH$_2$CH$_3$ | 5 | 81 | 4 h |
| 4[b] | Cy-CH(OAc)- | 5 | 89 | 17 h |
| 5[d] | Ph-CH(OTBS)-CH$_2$- | 2 | 92 | 35 min |
| 6 | R = C$_8$H$_{17}$ | 2 | 86 | 20 mm |
| 7[e] | R = C$_8$H$_{17}$ | 2 | 75 | 4 h |
| 8 | R = HOC$_9$H$_{18}$ | 2 | 98 | 35 min |
| 9[f] | R = HOC$_9$H$_{18}$ | 1 | 91 | 40 min |
| 10 | R = MeO$_2$CC$_8$H$_{16}$ | 2 | 87 | 35 min |
| 11 | (2,2-dimethyl-1,3-dioxolan-4-yl)propyl | 2 | 95 | 30 min |
| 12[d] | R = ClC$_9$H$_{18}$ | 2 | 89 | 80 min |
| 13 | R = 4-MePh | 5 | 88 | 50 min |
| 14[d] | R = 4-BOCNHPh | 5 | 83 | 60 min |
| 15[d] | R = 3-NO$_2$Ph | 5 | 60 | 17 h |

[a]Average isolated yield of two experiments performed on 3 mmol scale.
[b]Substrate added at room temperature.
[c]15 mol % AgSbF$_6$ used.
[d]1 mmol scale in a 25 mL round bottom flask.
[e]4 eq of TBHP used.
[f]One experiment performed on 20 mmol scale in a 250 mL round bottom flask, 1% catalyst and at 0.2 M.

Several common protecting groups for allylic alcohols were shown to be compatible with these conditions, providing the methyl ketone products in high yields (Table 1, entries 1-4). No aldehyde product was detected in any of these cases by GC or 1H NMR analysis. Thus, the above approach can be substantially free or completely free of undesired aldehyde products. Additionally, silyl protected allylic alcohols proceed to product at a significantly faster rate, allowing for the use of lower catalyst loadings (entry 2). An acetal-protecting group, was stable to Lewis acidic, aqueous reaction conditions (entry 3). A homoallylic alcohol also was converted to the methyl ketone in excellent yield (entry 5).

The corresponding ketones were each confirmed using NMR, IR and HRMS analyses. The 2-oxooctan-3-yl acetate, 3-(tert-butyldimethylsiloxy)octan-2-one, 3-(ethoxymethoxy)octan-2-one, 1-cyclohexyl-2-oxopropyl acetate, 4-(tert-butyldimethylsolxy)-4-phenylbutan-2-one, 2-decanone, methyl 10-oxoundecanoate, 6-(2,2-dimethyl-1,3-dioxolan-4-yl)hexan-2-one, 11-chloroundecan-2-one, 1-p- tolyethanone were recovered as colorless oils. The 11-hydroxyundecan-2-one, tert-butyl 4-acetylphenylcarbamate, and 1-(3-nitro)ethanone were recovered as a white solid having a melting point of 39-40° C., 113-114° C., and 68-70° C., respectively. Similarly, 11-hydroxyundecan-2-one was isolated as a white solid.

The catalytic system was further evaluated to determine whether it was a general catalyst for the Wacker oxidation. Excitingly, the current system rapidly consumes decene leading to 2-decanone in good yield with no appreciable amounts of internal isomers (entry 6). Lowering the amount of TBHP led to conversion of decene without significant loss of yield or increase in isomerization (entry 7). Other functional groups were evaluated including an alkene with a free distal alcohol, which was used to demonstrate the scalability of the reaction using a reduced catalyst loading (entries 8 and 9). Additionally, alkenes containing common functional groups including a methyl ester, acetonide, and primary chloride are well tolerated (entries 10-12). A number of styrene derivatives, another challenging substrate class for the Tsuji-Wacker oxidation, were also evaluated. Substituted styrenes with various functional groups were efficiently oxidized, although a highly electron-deficient system led to a lower yield and a trace amount of m-nitro benzaldehyde (entries 13-15). It should be noted that these reactions are exothermic; therefore the oxidations were initiated at 0° C.

An additional adamantane alkene substrate was tested. To a small 1.5 mL vial was weighed AgSbF$_6$ (3.9 mg, 0.01 mmol) and Pd(Quinox)Cl$_2$ (1.1 mg, 0.003 mmol). The solvent CH$_2$Cl$_2$ (64 µL) and a stirbar were added to the vial and the mixture was stirred for 10 min. TBHP (86 µL) was added to the flask and stirred for an additional 10 min. A solution of 1-ethenyladamantane (9.7 mg, 0.05 mmol) and dodecane (~1 mg as an internal standard for GC analysis) was made in CH$_2$Cl$_2$ (380 µL). An amount of 350 µL of the standard solution was used to add substrate to the reaction mixture while the remaining solution was used as an initial timepoint. A timepoint taken after 15 min indicated complete consumption of the starting material and a GC yield of 94% (measured relative to the internal standard and corrected for response factor). After 1 h the reaction mixture was worked up in the standard way and the product was isolated to confirm that the product was indeed the methyl ketone. Each of $^1$H NMR, $^{13}$C NMR, and GC-MS analysis all indicate exclusive formation of the methyl ketone in accordance with the published NMR data, with no aldehyde product observed. Further, dodecane was observed in the NMR spectra.

Evaluation of Enantiomeric Excess Retention:

Finally, to ascertain the applicability of this method to target synthesis, enantioenriched protected allylic and homoallylic alcohols were oxidized under the optimal conditions with no loss of enantiomeric excess according to the following equations

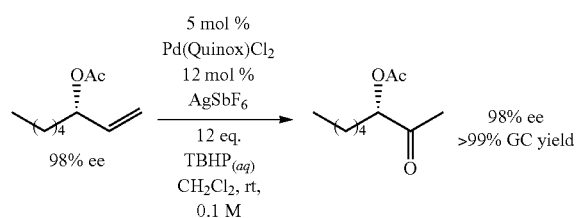

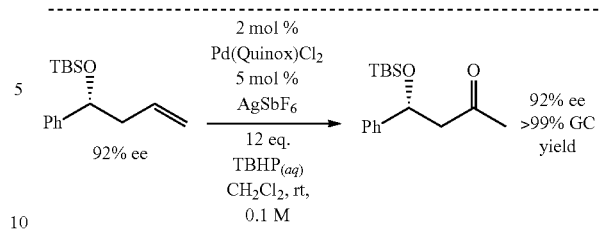

To 2 mL brown screw cap vials was weighed AgSbF$_6$ (0.012 mmol and 0.006 mmol respectively) followed by a specified volume of a Pd(quinox)Cl$_2$ (0.005 mmol and 0.002 mmol respectively) standard solution and the mixtures were stirred for ~15 min. 70 wt % TBHP$_{(aq)}$ (1.2 mmol, 172 µL) was added to the vials and stirred for an additional 10 min, at which time the enantiomerically enriched substrates (0.1 mmol, 98% ee and 92% ee respectively) were added as standard solutions so that the concentration of the reaction would be 0.1 M. Alliquots (~50 µL) of the reaction mixture were taken periodically, run through a small silica pipet with ethyl acetate, and analyzed for conversion, product formation, and enantiomeric excess by chiral phase gas chromatography as shown in Table 2 of chiral separations.

TABLE 2

| compound | method | retention times (min) |
|---|---|---|
| OAc, C$_5$H$_{11}$, alkene | hold 100° C. 25 min | 6.5/6.9 |
| OAc, C$_5$H$_{11}$, ketone | hold 100° C. 25 min | 19.9/20.8 |
| TBSO, Ph, alkene | hold 80° C. 150 min | 45.1/45.8 |
| TBSO, Ph, ketone | hold 100° C. 150 min | 135.2/143.0 |

GC column: HP-Chiral 20% permethylated β-cyclodextrin

In conclusion, the above examples demonstrate a practical general method for Wacker oxidation, which exhibits short reaction times, uses an inexpensive oxidant, can tolerate previously challenging substrates, and provides products selectively in high yields. Of particular interest is the exceptional performance of the Quinox ligand, which is rapidly synthesized in two steps, as compared with the other bidentate nitrogen ligands evaluated. The ligand framework is also highly modular, which can allow effective design of substrate and reaction choices.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A method of catalytically oxidizing an alkene, comprising:
   a) exposing an alkene to a quinoline catalyst complex in the presence of a mediation compound to form a ketone, said quinoline catalyst complex including a coordination center complexed with a quinoline compound having the formula

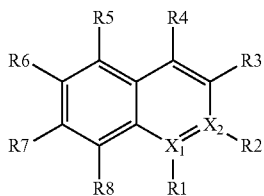

where one of $X_1$ and $X_2$ is an N and the other is C and one of R1, R2 and R3 is Z wherein Z is an oxazoline having the formula

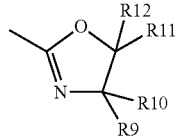

such that when $X_1$ is N R2 is Z and R1 is absent, and when $X_2$ is N either R1 or R3 is Z and R2 is absent, and R1 and R3 through R12 are independently H or a pendant moiety which does not interfere with coordination of either N in the quinoline compound with the coordination center.

2. The method of claim 1, wherein the quinoline compound is a quinoline-2-oxazoline having the formula:

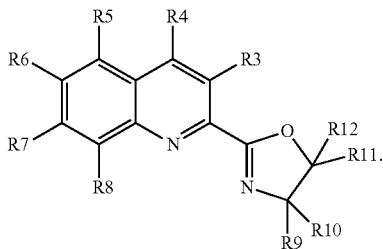

3. The method of claim 2, wherein R3 through R12 are hydrogen.

4. The method of claim 2, wherein R3 through R8, R11 and R12 are hydrogen and R9 and R10 are methyl.

5. The method of claim 1, wherein the quinoline compound is a 1-isoquinolineoxazoline having the formula:

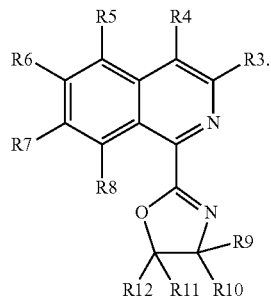

6. The method of claim 5, wherein R3 through R12 are hydrogen.

7. The method of claim 1, wherein the quinoline compound is a 3-isoquinolineoxazoline having the formula:

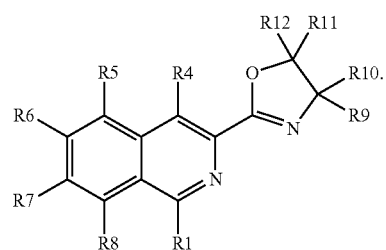

8. The method of claim 7, wherein R1 and R4 through R12 are hydrogen.

9. The method of claim 1, wherein R1 and R3 through R12 are independently selected from the group consisting of hydrogen, lower alkyl, aryl, and halide.

10. The method of claim 9, wherein R1 and R3 through R12 are each hydrogen.

11. The method of claim 9, wherein at least one of R1 and R3 through R12 is methyl.

12. The method of claim 11, wherein R9 and R10 are methyl.

13. The method of claim 9, wherein at least one of R1 and R3 through R12 is a lower alkyl having up to 8 carbon atoms.

14. The method of claim 9, wherein at least one of R1 and R3 through R12 is aryl.

15. The method of claim 9, wherein at least one of R1 and R3 through R12 is a halide selected from the group consisting of fluorine, chlorine and bromine.

16. The method of claim 1, wherein the quinolone catalyst complex further comprising the coordination center coordinated with each of the N in the quinoline compound.

17. The method of claim 16, wherein the coordination center is a metal.

18. The method of claim 17, wherein the metal is palladium, platinum, rhodium or nickel.

19. The method of claim 18, wherein the palladium is palladium (II).

20. A quinoline compound having the formula:

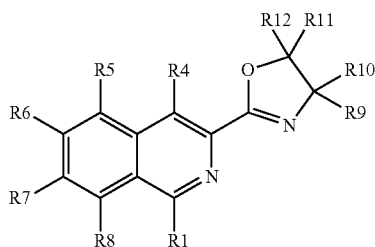

wherein R1 and R4 through R12 are hydrogen.

21. A quinoline compound having the formula:

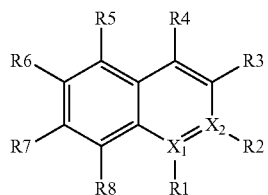

where one of $X_1$ and $X_2$ is an N and the other is C and one of R1, R2 and R3 is Z wherein Z is an oxazoline radical having the formula

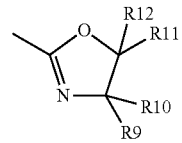

such that when $X_1$ is N R2 is Z and R1 is absent, and when $X_2$ is N either R1 or R3 is Z and R2 is absent, and R1 and R3 through R12 are independently H or a pendant moiety which does not interfere with coordination of either N in the quinoline compound with a coordination center and at least one of R1 and R3 through R12 is a halide selected from the group consisting of fluorine, chlorine and bromine.

* * * * *